(12) United States Patent
Sizov

(10) Patent No.: US 12,146,849 B2
(45) Date of Patent: *Nov. 19, 2024

(54) ETHYLENE RECEPTOR BIOSENSOR

(71) Applicant: Strella Biotechnology, Inc., Wilmington, DE (US)

(72) Inventor: Katherine Konstantin Sizov, Philadelphia, PA (US)

(73) Assignee: Strella Biotechnology Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/134,790

(22) Filed: Apr. 14, 2023

(65) Prior Publication Data
US 2024/0060929 A1 Feb. 22, 2024

Related U.S. Application Data

(63) Continuation of application No. 16/798,375, filed on Feb. 23, 2020, now Pat. No. 11,662,330, which is a continuation of application No. PCT/US2019/062253, filed on Nov. 19, 2019, which is a continuation-in-part of application No. PCT/US2019/032731, filed on May 16, 2019, said application No. 16/798,375 is a continuation-in-part of application No. PCT/US2019/032731, filed on May 16, 2019.

(60) Provisional application No. 62/674,639, filed on May 22, 2018.

(51) Int. Cl.
| | | |
|---|---|---|
| G01N 27/327 | (2006.01) |
| A61B 5/1486 | (2006.01) |
| C07K 14/415 | (2006.01) |
| G01N 27/07 | (2006.01) |
| G01N 27/404 | (2006.01) |
| G01N 33/00 | (2006.01) |
| G01N 33/02 | (2006.01) |
| G01N 33/53 | (2006.01) |
| G01N 33/543 | (2006.01) |

(52) U.S. Cl.
CPC ....... *G01N 27/3275* (2013.01); *A61B 5/1486* (2013.01); *C07K 14/415* (2013.01); *G01N 27/07* (2013.01); *G01N 27/3276* (2013.01); *G01N 27/4045* (2013.01); *G01N 33/5302* (2013.01); *G01N 33/5308* (2013.01); *G01N 33/5438* (2013.01); *G01N 33/0047* (2013.01); *G01N 33/025* (2013.01)

(58) Field of Classification Search
None
See application file for complete search history.

(56) References Cited

U.S. PATENT DOCUMENTS 11,662,330 B2 * 5/2023 Sizov ................. G01N 33/5302
205/792
2005/0272989 A1 * 12/2005 Shah ...................... C12Q 1/006
600/347

FOREIGN PATENT DOCUMENTS

KR 1020150134157 A1 * 12/2015

* cited by examiner

*Primary Examiner* — J. Christopher Ball
(74) *Attorney, Agent, or Firm* — Charney IP Law, LLC; Thomas M. Finetti

(57) ABSTRACT

The present disclosure relates to biosensors (10) having a receptor layer (5) and a mediator layer (6), the receptor layer including ethylene receptor molecules. The present disclosure also relates to sensor units (20) comprising one or more biosensors (10) and a controller (11). In some embodiments, one or more sensor units (20) may be in wireless communication with a receiver module or a network gateway.

20 Claims, 10 Drawing Sheets
Specification includes a Sequence Listing.

SEQUENCE LISTING

```
Sequence total quantity: 4
SEQ ID NO: 1           moltype = AA  length = 738
FEATURE                Location/Qualifiers
REGION                 1..738
                       note = misc_feature - ETHYLENE RECEPTOR 1 (ETR1)
source                 1..738
                       mol_type = protein
                       organism = Arabidopsis thaliana
SEQUENCE: 1
MEVCNCIEPQ WPADELLMKY QYISDFFIAI AYFSIPLELI YFVKKSAVFP YRWVLVQFGA   60
FIVLCGATHL INLWTFTTHS RTVALVMTTA KVLTAVVSCA TALMLVHIIP DLLSVKTREL  120
FLKNKAAELD REMGLIRTQE ETGRHVRMLT HEIRSTLDRH TILKTTLVEL GRTLALEECA  180
LWMPTRTGLE LQLSYTLRHQ HPVEYTVPIQ LPVINQVFGT SRAVKISPNS PVARLRPVSG  240
KYMLGEVVAV RVPLLHLSNF QINDWPELST KRYALMVLML PSDSARQWHV HELELVEVVA  300
DQVAVALSHA AILEESMRAR DLLMEQNVAL DLARREAETA IRARNDPLAV MNHEMRTPMH  360
AIIALSSLLQ ETELTPEQRL MVETILKSSN LLATLMNDVL DLSRLEDGSL QLELGTFNLH  420
TLFREVLNLI KPIAVVKKLP ITLNLAPDLP EFVVGDEKRL MQIILNIVGN AVKFSKQGSI  480
SVTALVTKSD TRAADFFVVP TGSHFYLRVK VKDSGAGINP QDIPKIFTKF AQTQSLATRS  540
SGGSGLGLAI SKRFVNLMEG NIWIESDGLG KGCTAIFDVK LGISERSNES KQSGIPKVPA  600
IPRHSNFTGL KVLVMDENGV SRMVTKGLLV HLGCEVTTVS SNEECLRVVS HEHKVVFMDV  660
CMPGVENYQI ALRIHEKFTK QRHQRPLLVA LSGNTDKSTK EKCMSFGLDG VLLKPVSLDN  720
IRDVLSDLLE PRVLYEGM                                                738

SEQ ID NO: 2           moltype = AA  length = 773
FEATURE                Location/Qualifiers
REGION                 1..773
                       note = misc_feature - ETHYLENE RECEPTOR 2 (ETR2)
source                 1..773
                       mol_type = protein
                       organism = Arabidopsis thaliana
SEQUENCE: 2
MVKEIASWLL ILSMVVFVSP VLAINGGGYP RCNCEDEGNS FWSTENILET QRVSDFLIAV   60
```

```
AYFSIPIELL YFVSCSNVPF KWVLFEFIAF IVLCGMTHLL HGWTYSAHPF RLMMAFTVFK    120
MLTALVSCAT AITLITLIPL LLKVKVREFM LKKKAHELGR EVGLILIKKE TGFHVRMLTQ    180
EIRKSLDRHT ILYTTLVELS KTLGLQNCAV WMPNDGGTEM DLTHELRGRG GYGGCSVSME    240
DLDVVRIRES DEVNVLSVDS SIARASGGGG DVSEIGAVAA IRMPMLRVSD FNGELSYAIL    300
VCVLPGGTPR DWTYQEIEIV KVVADQVTVA LDHAAVLEES QLMREKLAEQ NRALQMAKRD    360
ALRASQARNA FQKTMSEGMR RPMHSILGLL SMIQDEKLSD EQKMIVDTMV KTGNVMSNLV    420
GDSMDVPDGR FGTEMKPFSL HRTIHEAACM ARCLCLCNGI RFLVDAEKSL PDNVVGDERR    480
VFQVILHIVG SLVKPRKRQE GSSLMFKVLK ERGSLDRSDH RWAAWRSPAS SADGDVYIRF    540
EMNVENDDSS SQSFASVSSR DQEVGDVRFS GGYGLGQDLS FGVCKKVVQL IHGNISVVPG    600
SDGSPETMSL LLRFRRRPSI SVHGSSESPA PDHHAHPHSN SLLRGLQVLL VDTNDSNRAV    660
TRKLLEKLGC DVTAVSSGFD CLTAIAPGSS SPSTSFQVVV LDLQMAEMDG YEVAMRIRSR    720
SWPLIVATTV SLDEEMWDKC AQIGINGVVR KPVVLRAMES ELRRVLLQAD QLL           773

SEQ ID NO: 3           moltype = AA  length = 836
FEATURE                Location/Qualifiers
REGION                 1..836
                       note = misc_feature - ETHYLENE RECEPTOR 3 (ETR3) of Oryza
                         sativa indica (RICE)
source                 1..836
                       mol_type = protein
                       organism = Oryza sativa
SEQUENCE: 3
MLLSTWTPGC FQGNKILLRS LITWYYLEFM PKLRPFYFLF YLTLPSCATD SPPISDKSSS     60
IFLPLAQQQQ LVHWMMPPRF RCQDYLLPLL LALSPAAAAA REVEYHHCHC DGGGGGGGGG    120
LWSMDSIFRR QKVSDLLIAA AYFSIPLEIL YFVAGLRHLL PFRWVLVQFG AFIVLCGLTH    180
LLTAFTYEPH PFMVVLLLTT AKFLTALVSF LTAITLLTIL PQLLRVKVRE SLLWLKAREL    240
DREVVLMKRQ EEASWHVRML THEIRKSLDR HTVLYTTLIE LSLVLGLTNC AVWMPAAGEM    300
CLTHELRRDG GGEDGVVGVD DADVVEVRGS DGVKLLGPDS VLAAASGGKE EGTGAVAAIR    360
MPMLKVSDFK GGTPEVIQTS YAVLVLVPPA GKSWGRHEME IVEVVAGQVA VALSHATLLE    420
ESRAMRDRLA EQNRELLQAR RDALMANEAR QAFQGVMSQG MRRPIHSILG LVSMVQEEAL    480
APEQRLVVDT MARTATVVST LVNDVMEMSA DSRERFPLET RPFHLHAMIR DAACVARCLC    540
DFRGFGFAVH VENALPDLVV GDERRIFHVL LHMVGNLIGR TEPGHVTLRV RAADDDVLDD    600
RLGQRWDPRW PSYSTGYSSV KFVIGVKRQQ NGDAGSPLSR RPSGKGIDLR LSFSMCRKLV    660
QMMQGNIWAI NDPQGLPESM TLVLRFQLQS PLTSSSLGSS FEQKHSSPSC QIAGLKVLLI    720
DDDDDINLVV ARKLLEKLGC VVSSPPSGSG FLSSVGSSAA AFQLVMVNLE MKRVKALDVA    780
TRISQYRSGR WPIVMAMASD QKAWEKCAQS GINGILKKPV ILQELKDELA RILQST        836

SEQ ID NO: 4           moltype = AA  length = 777
FEATURE                Location/Qualifiers
REGION                 1..777
                       note = misc_feature - ETHYLENE RECEPTOR 4 (ETR4) of Oryza
                         sativa japonica (RICE)
source                 1..777
                       mol_type = protein
                       organism = Oryza sativa
SEQUENCE: 4
MAMVTARQFL ASAAELGSGR RRCGGGGACD MREDGGVEAL MQCQRVSDLL IAASFLSIPL     60
ELFYFATCAD LSEVKCAVLH FCAFIVLCGA THLLAAFTHA HPHSAPLLRA LTAAKVLAAV    120
ASSAAAVSLL TFIPKLLRIK VRESLLRDKA SRLHRDLGLV RRREEATSRA VRELTGRIRA    180
SPPDAHAILR TTALQLADAL GLHACAVWMP AAGRPHDLVL VHHLTSRPDD AADLLLEVGD    240
ACTVAADDPD VVDVMASKVA KVLGPDSALA MASSVGAAPA GAVAAIRIPI LRVSIYDGGG    300
TPEVTEASYA ILVLLLPPHD AAGGWSSHDL EIVQVVADQA AVALSHAAVL EESRSMRDRF    360
AEQHRALMQA KHRAAMATRA FSSIQSAMCH AMRRPVHSVV GLVSMLQHPE ADTMRPEQRL    420
AVDAIARTSN LLSALMDEVT VNRQHLSVQR KPFSLHALIK EAISVAGCLS HCGGAGFLHQ    480
PECALPEWVV GDERRVFHLL LDMVGTLLNR CNTGSGACRL SFSVRICNVG EERYSLDWIP    540
MRPTFSGCNV CVKFKVGIGR SRSCAIERSL PCELPRRSAA TTSSQMGHIF SGYFNKIVQM    600
MNGNMWSASD SEGVGESVTL ILQFKLQQGH VEASPPYIPH LNGLRVLLAD DDAMNRGVTK    660
KILERLGCQV MSAPSGAHCL SLLASAEASF QLVVLDLDDR AVPSAAMDRF EVALRIRELR    720
NSCWLLIVIA VAAGVVATDD GGAVQELCQR AGINGLVQKP VTLPALGAQL CRVLQDN       777
```

ETHYLENE RECEPTOR BIOSENSOR

CROSS REFERENCE TO RELATED APPLICATIONS

The present disclosure is a continuation of U.S. patent application Ser. No. 16/798,375 filed on Feb. 23, 2020, which application is a continuation of International Application No. PCT/US19/62253 filed on Nov. 19, 2019, which application claims the benefit of the filing date of International Application No. PCT/US19/32731 filed on May 16, 2019, which application claims the benefit of the filing date of U.S. Provisional Patent Application No. 62/674,639 filed on May 22, 2018; the present disclosure is a continuation of U.S. patent application Ser. No. 16/798,375 filed on Feb. 23, 2020, which application is a continuation-in-part of International Application No. PCT/US19/32731 filed on May 16, 2019, which application claims the benefit of the filing date of U.S. Provisional Patent Application No. 62/674,639 filed on May 22, 2018, the disclosures of which are hereby incorporated by reference herein in their entireties.

BACKGROUND OF THE DISCLOSURE

There is a continuing trend throughout the world toward consumption of fresher and minimally processed food. High quality fresh fruits and vegetables are now available year round, thanks to improved packaging, storage technologies and rapid global transportation. The abundance of year-round fresh produce is dependent on a vast infrastructure including specialized refrigerated storage facilities.

Maintaining the freshness of fruit, vegetables, and other horticultural products, such as fresh cut flowers, is important to the postharvest industry and producers during various stages of transportation and storage. One of the ways to control the freshness of produce is by regulating its exposure to ethylene.

Ethylene is a plant hormone that has a role in many plant development mechanisms. Importantly, it plays a function in the ripening of climacteric fruits in an autocatalytic manner. As fruit ripens, it emits increased concentrations of ethylene, and can be a predictor for the maturity of produce. When produce has a limited exposure to ethylene, its natural aging process will be slowed. Ethylene emissions by fruits, vegetables and flowers occur in a variant-dependent, predictable manner (Watkins 1989; Chu 1984; Chu 1988; Diley 1980; Knee et al. 1983; Perring & Pearson 1986). With a high-accuracy measurement of ethylene, one can predict the stage of ripening and senescence a climacteric fruit is in. Thus, the measurement of ethylene allows for the prediction of ripening before it occurs. This allows for adjustments to be made within the supply chain to prevent food waste. For example, apples are stored in controlled atmosphere (CA) storage rooms for months after they are picked. Determining the proper order in which to pack a CA room for consumption further down the supply chain can minimize food waste and increase produce quality. Such optimization can be performed with a high accuracy ethylene sensor.

The most basic existing technology for ethylene measurement is to obtain an air sample, then later test it at one's convenience for ethylene concentrations under laboratory conditions. For example, an air sample may be gathered in a sample bag and sent to a lab for gas chromatography testing. This technique provides an accurate measurement of ethylene within the conditions of the sample collection. Due to the cumbersome nature of the process, this technique is not practical for continuous ethylene monitoring. One drawback to this technique is that the ethylene concentration is not known in real time—there is a delay associated with the sampling and testing. Additionally, a single sample does not permit for the predictive capabilities ethylene sensing can provide; that is, one cannot make a prediction regarding fruit senescence with infrequent and delayed data points.

Another current technology for ethylene measurement is to use a sampling pump to draw air through a detector tube. When air is pumped over the detector tube, the concentration of a particular gas is indicated. This is normally done by means of a color change shown on graduations along the side of the detection tube. The detection tube can be exposed to air either by means of a hand pump (such as Sensidyne's AP-1S) or by a mechanical pump that draws air more slowly across the detection tube, to provide a reading averaged over a longer period (such as Sensidyne's GilAir5).

The resolution of this technique is only as good as one can read the color change and tends to be accurate within 100 ppm. Such low resolution does not permit for the detection of subtle changes, such as fruit maturity or senescence within the sample. This technique is also limited due to its single-use, disposable tubes.

BRIEF SUMMARY OF THE DISCLOSURE

In one aspect of the present disclosure is a biosensor comprising: (a) a reference electrode including (i) a mediator layer in communication with a base electrode; and (ii) a receptor layer in communication with the mediator layer, wherein the receptor layer comprises an ethylene receptor; and (b) a working electrode in communication with the reference electrode. In some embodiments, the base electrode is comprised of a material selected from the group consisting of copper and silver. In some embodiments, the base electrode comprises a coating of a material selected from the group consisting of copper and gold. In some embodiments, the reference electrode and the working electrode are formed or deposited on the same substrate. In some embodiments, the biosensor further comprises a counter electrode.

In some embodiments, the ethylene receptor is at least 90% identical to a wild-type polynucleotide sequence of an ethylene receptor gene. In some embodiments, the ethylene receptor is at least 95% identical to a wild-type polynucleotide sequence of an ethylene receptor gene. In some embodiments, the ethylene receptor is at least 97% identical to a wild-type polynucleotide sequence of an ethylene receptor gene. In some embodiments, the ethylene receptor is at least 98% identical to a wild-type polynucleotide sequence of an ethylene receptor gene. In some embodiments, the ethylene receptor is at least 99% identical to a wild-type polynucleotide sequence of an ethylene receptor gene. In some embodiments, the ethylene receptor is derived from *Zea mays* or *Arabidopsis*. In some embodiments, the ethylene receptor comprises an amino acid sequence having at least 90% identity to that of SEQ ID NO: 1. In some embodiments, the ethylene receptor comprises an amino acid sequence having at least 90% identity to that of SEQ ID NO: 2. In some embodiments, the ethylene receptor comprises an amino acid sequence having at least 90% identity to that of SEQ ID NO: 3. In some embodiments, the ethylene receptor comprises an amino acid sequence having at least 90% identity to that of SEQ ID NO: 4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a stack comprising: (a) a mediator layer, and (b) a receptor layer in contact with the mediator layer, wherein the receptor layer comprises an ethylene receptor protein. In some embodiments, the ethylene receptor protein has an amino acid sequence having at least 95% identity to any of the ethylene receptor proteins selected from the group consisting of ETR1, ETR2, ETR3, and ETR4. In some embodiments, the ethylene receptor protein is selected from the group consisting of ETR1, ETR2, ETR3, and ETR4. In some embodiments, the ethylene receptor protein comprises an amino acid sequence having at least 85% identity to any one of SEQ ID NOS: 1-4. In some embodiments, the ethylene receptor protein comprises an amino acid sequence having at least 90% identity to any one of SEQ ID NOS: 1-4. In some embodiments, the ethylene receptor protein comprises an amino acid sequence having at least 95% identity to any one of SEQ ID NOS: 1-4. In some embodiments, the ethylene receptor protein comprises an amino acid sequence having at least 96% identity to any one of SEQ ID NOS: 1-4. In some embodiments, the ethylene receptor protein comprises an amino acid sequence having at least 97% identity to any one of SEQ ID NOS: 1-4. In some embodiments, the ethylene receptor protein comprises an amino acid sequence having at least 98% identity to any of SEQ ID NOS: 1-4. In some embodiments, the ethylene receptor protein comprises an amino acid sequence having at least 99% identity to any one of SEQ ID NOS: 1-4. In some embodiments, the ethylene receptor protein comprises an amino acid sequence having any one of SEQ ID NOS: 1-4. In some embodiments, between about 0.0005 mg/mm to about 1.75 mg/mm of ethylene receptor are protein are included within the receptor layer. In some embodiments, between about 0.0008 mg/mm to about 1.55 mg/mm of ethylene receptor are protein are included within the receptor layer. In some embodiments, between about 0.1 to about 0.8 mg/mm of ethylene receptor are protein are included within the receptor layer. In some embodiments, between about 0.9 to about 1.6 mg/mm of ethylene receptor are protein are included within the receptor layer. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a reference electrode comprising a stack deposited on a base electrode, wherein the stack comprises (a) a mediator layer, and (b) a receptor layer in contact with the mediator layer, wherein the receptor layer comprises an ethylene receptor protein. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4 . . . . In some embodiments, the ethylene receptor protein comprises an amino acid sequence having at least 95% identity to any one of SEQ ID NOS: 1-4. In some embodiments, the ethylene receptor protein comprises an amino acid sequence having at least 96% identity to any one of SEQ ID NOS: 1-4. In some embodiments, the ethylene receptor protein comprises an amino acid sequence having at least 97% identity to any one of SEQ ID NOS: 1-4. In some embodiments, the ethylene receptor protein comprises an amino acid sequence having at least 98% identity to any one of SEQ ID NOS: 1-4. In some embodiments, the ethylene receptor protein comprises an amino acid sequence having at least 99% identity to any one of SEQ ID NOS: 1-4. In some embodiments, the ethylene receptor protein comprises an amino acid sequence having any one of SEQ ID NOS: 1-4. In some embodiments, between about 0.0005 mg/mm to about 1.75 mg/mm of ethylene receptor are protein are included within the receptor layer. In some embodiments, between about 0.0008 mg/mm to 1.55 mg/mm of ethylene receptor are protein are included within the receptor layer. In some embodiments, between about 0.1 to about 0.8 mg/mm of ethylene receptor are protein are included within the receptor layer. In some embodiments, between about 0.9 to about 1.6 mg/mm of ethylene receptor are protein are included within the receptor layer. In some embodiments, the base electrode is a metal electrode. In some embodiments, the metal electrode is comprised of copper or silver. In some embodiments, the base electrode comprises a coating including copper or silver. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a biosensor comprising (i) a reference, and; and (ii) a working electrode in communication with the reference electrode; wherein the reference electrode comprises a stack deposited on a metal electrode, wherein the stack comprises (a) a mediator layer, and (b) a receptor layer in contact with the mediator layer, wherein the receptor layer comprises an ethylene receptor protein. In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the reference electrode and the working electrode are both formed or deposited on the same substrate. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a sensor unit comprising (i) one or more biosensors, and (ii) a controller in communication with the one or more biosensors; wherein the biosensor includes a reference electrode in communication with a working electrode, the reference electrode having a stack deposited on an electrode, wherein the stack includes (a) a mediator layer, and (b) a receptor layer in contact with the mediator layer, wherein the receptor layer comprises an ethylene receptor protein. In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole. In some embodiments, the controller comprises a communication module. In some embodiments, the communication module is a wireless communication module.

In another aspect of the present disclosure is a sensor unit comprising (1) one or more biosensors, and (2) a controller in communication with the one or more biosensors; wherein the biosensor includes (a) a reference electrode including (i) a mediator layer deposited on a metal electrode; and (ii) a receptor layer deposited on the mediator layer, wherein the receptor layer comprises an ethylene receptor; and (b) a working electrode in communication with the reference electrode. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole. In some embodiments, the controller comprises a communication module. In some embodiments, the communication module is a wireless communication module.

In another aspect of the present disclosure is a system comprising a plurality of the sensor units described above, wherein the plurality of sensor units are each independently in wireless communication with a receiver module, a gateway, or a storage module.

In another aspect of the present disclosure is a container comprising at least one of the sensor units described above. In some embodiments, each container is in wireless communication with a receiver module, a gateway, or a storage module.

In another aspect of the present disclosure is a method of detecting the presence of ethylene using any of the biosensors or sensor units described above. In some embodiments, a quantitative measurement of an ethylene concentration may be made using any of the biosensors or sensor units described above.

In another aspect of the present disclosure is a biosensor comprising: (a) a reference electrode including (i) a mediator layer in communication with a base electrode; and (ii) a receptor layer in communication with the mediator layer, wherein the receptor layer comprises an ethylene receptor; (b) a working electrode in communication with the reference electrode; and (c) a counter electrode. In some embodiments, the base electrode is comprised of a material selected from the group consisting of copper and silver. In some embodiments, the base electrode comprises a coating of a material selected from the group consisting of copper and gold. In some embodiments, the reference electrode and the working electrode are formed or deposited on the same substrate.

In some embodiments, the ethylene receptor is at least 90% identical to a wild-type polynucleotide sequence of an ethylene receptor gene. In some embodiments, the ethylene receptor is at least 95% identical to a wild-type polynucleotide sequence of an ethylene receptor gene. In some embodiments, the ethylene receptor is at least 97% identical to a wild-type polynucleotide sequence of an ethylene receptor gene. In some embodiments, the ethylene receptor is at least 98% identical to a wild-type polynucleotide sequence of an ethylene receptor gene. In some embodiments, the ethylene receptor is at least 99% identical to a wild-type polynucleotide sequence of an ethylene receptor gene. In some embodiments, the ethylene receptor is derived from *Zea mays* or *Arabidopsis*. In some embodiments, the ethylene receptor comprises an amino acid sequence having at least 90% identity to that of SEQ ID NO: 1. In some embodiments, the ethylene receptor comprises an amino acid sequence having at least 90% identity to that of SEQ ID NO: 2. In some embodiments, the ethylene receptor comprises an amino acid sequence having at least 90% identity to that of SEQ ID NO: 3. In some embodiments, the ethylene receptor comprises an amino acid sequence having at least 90% identity to that of SEQ ID NO: 4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a biosensor comprising (i) a reference, and; (ii) a counter electrode; and (iii) a working electrode in communication with the reference electrode; wherein the reference electrode comprises a stack deposited on a metal electrode, wherein the stack comprises (a) a mediator layer, and (b) a receptor layer in contact with the mediator layer, wherein the receptor layer comprises an ethylene receptor protein. In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the reference electrode and the working electrode are both formed or deposited on the same substrate. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a sensor unit comprising (i) one or more biosensors, and (ii) a controller in communication with the one or more biosensors; wherein the biosensor includes a counter electrode, and reference electrode in communication with a working electrode, the reference electrode having a stack deposited on an electrode, wherein the stack includes (a) a mediator layer, and (b) a receptor layer in contact with the mediator layer, wherein the receptor layer comprises an ethylene receptor protein. In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole. In some embodiments, the controller comprises a communication module. In some embodiments, the communication module is a wireless communication module.

In another aspect of the present disclosure is a sensor unit comprising (1) one or more biosensors, and (2) a controller in communication with the one or more biosensors; wherein the biosensor includes (a) a reference electrode including (i) a mediator layer deposited on a metal electrode; and (ii) a receptor layer deposited on the mediator layer, wherein the receptor layer comprises an ethylene receptor; (b) a working electrode in communication with the reference electrode; and (c) a counter electrode. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole. In some embodiments, the controller comprises a communication module. In some embodiments, the communication module is a wireless communication module.

In another aspect of the present disclosure is a system comprising a plurality of the sensor unit, including any sensor unit incorporating a three-electrode design, wherein the plurality of sensor units are each independently in wireless communication with a receiver module, a gateway, or a storage module.

In another aspect of the present disclosure is a container comprising at least one of the sensor units described above, including any sensor unit incorporating a three-electrode design. In some embodiments, each container is in wireless communication with a receiver module, a gateway, or a storage module.

In another aspect of the present disclosure is a method of detecting the presence of ethylene using any of the biosensors or sensor units described above, including any biosensor or sensor unit incorporating a three-electrode design. In some embodiments, a quantitative measurement of an ethylene concentration may be made using any of the biosensors or sensor units described above.

SEQUENCE LISTING

The contents of the electronic sequence listing (Strella-002US4.xml; Size: 9,260 bytes; and Date of Creation: Apr. 5, 2023) is herein incorporated by reference in its entirety.

BRIEF DESCRIPTION OF THE FIGURES

For a general understanding of the features of the disclosure, reference is made to the drawings. In the drawings, like reference numerals have been used throughout to identify identical elements.

DETAILED DESCRIPTION

Figure 1:
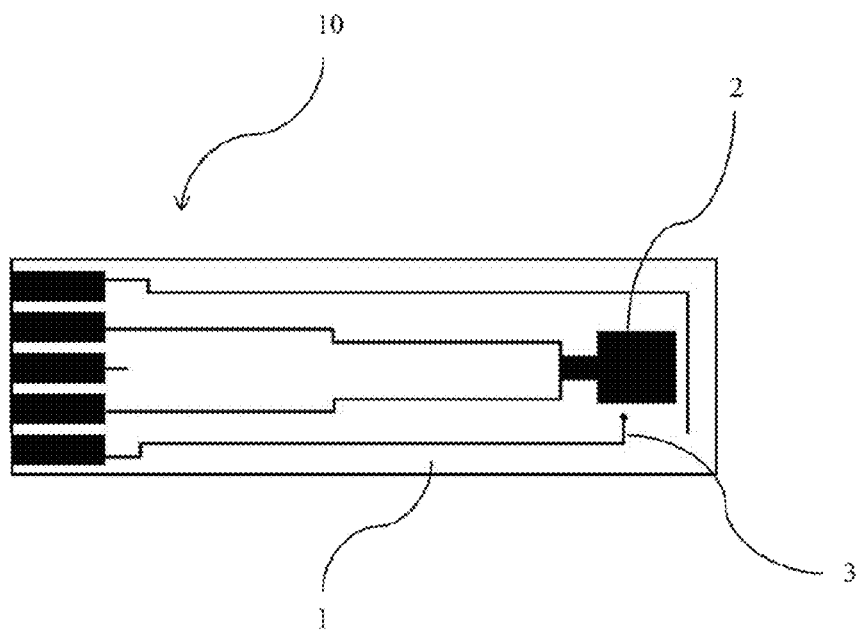
FIG. 1 illustrates a top down view of a biosensor in accordance with one embodiment of the present disclosure.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The present disclosure is directed to a biosensor comprising a reference electrode and a working electrode, wherein the reference electrode includes a layer comprising ethylene receptor molecules.

FIG. 1 depicts a top-down view of a biosensor 10 in accordance with one embodiment of the present disclosure. In some embodiments, the biosensor 10 includes a reference electrode 2 and a working electrode 3. In some embodiments, the reference electrode 2 and the working electrode 3 are provided on substrate 1. In some embodiments, substrate 1 is a non-conductive substrate, such as a fiberglass epoxy resin or a phenolic resin. In some embodiments, the substrate is selected from carbon, fiberglass epoxy resin, phenolic resin, insulated metal substrate, polyimide film and fluoropolymer/polyimide film composites. In some embodiments, the biosensor 10 further comprises one or more leads, so as to allow the biosensor to communicate with other components and/or devices. In some embodiments, the leads are comprised of conductive tracks within the substrate, connecting to the reference electrode surface and the working electrode. In some embodiments, the leads are comprised of the same metal in which the electrode is comprised. In some embodiments, the biosensor depicted in FIG. 1 includes one or more additional traces or leads.

Figure 8:
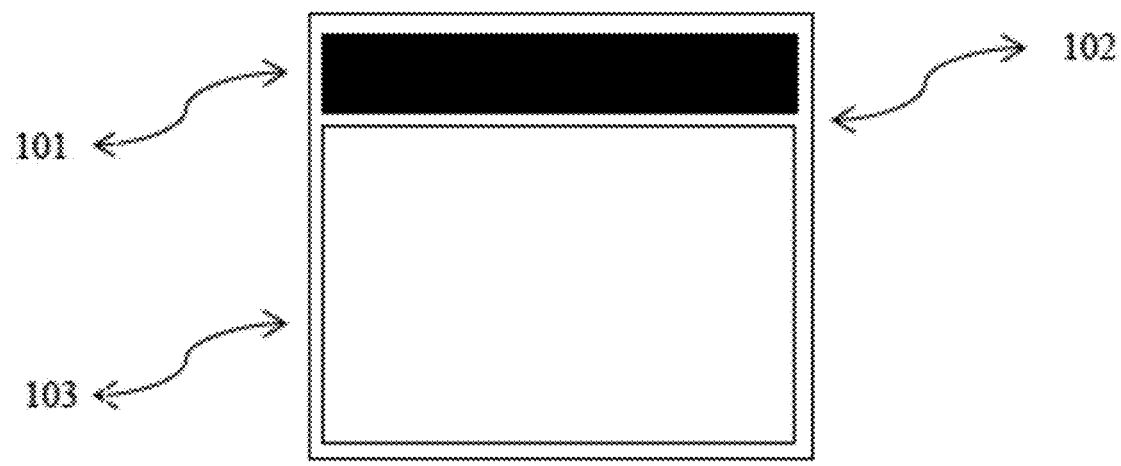
FIG. 8 illustrates a two-electrode system in accordance with one embodiment of the present disclosure.

FIG. 8 sets forth a top down schematic of a two-electrode system in accordance with one embodiment of the present disclosure. In some embodiments, a reference electrode 101 having a metal composition which differs from the working electrode 103 is separated by a gap 102. In some embodiments, an electrolytic mediator layer is posited proximal (e.g. atop) the two electrodes. Without wishing to be bound by any particular theory, it is believed that the electrolytic mediator layer promotes electron transfer between the reference electrode 101 and the working electrode 103. In some embodiments, and upon a reaction between the ethylene receptor and ethylene (such as described herein), an oxidation reduction reaction catalyzes the movement of electrons from one electron to the other, which can be measured via current or voltage changes.

Figure 9:
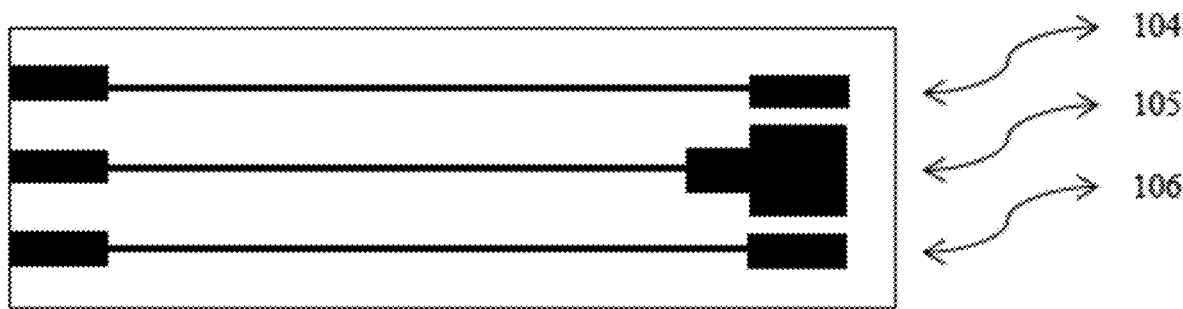
FIG. 9 illustrates a three-electrode system in accordance with the present disclosure.

FIG. 9 sets forth a top down schematic of a three-electrode system in accordance with another embodiment of the present disclosure. In some embodiments, the three-electrode system consists of three electrodes: a counter electrode 105, a reference electrode 104, and a working electrode 106. In some embodiments, the counter electrode 105 includes an ethylene receptor protein (including any of those described herein). In some embodiments, it is believed that the ethylene receptor protein undergoes a reduction and oxidation reaction upon contact with one or more ethylene molecules, such as those ethylene molecules present in an environment (e.g. an environment surrounding the biosensor). In some embodiments, this is believed to generate an electrical potential between the counter electrode 105 and the working electrode 106. In some embodiments, an electrolytic mediator layer is positioned proximal (e.g. atop) the two electrodes and is believed to promote electron transfer between the counter and working electrodes 105 and 106, respectively. In some embodiments, the measured current is believed to pass through the counter electrode and the third electrode, the working electrode. In some embodiments, an electrolytic solution in the form of the mediator layer is in contact (e.g. placed between) at least two of the electrodes, e.g. all three of the electrodes, to provide ions to the electrodes during the oxidation and reduction reaction between ethylene and the ethylene receptor protein.

In some embodiments, a three-electrode system permits stability advantages over the two-electrode system. With three electrodes, one can supply an external potential to the system, eliminating a variable. Theoretically, in a two-electrode system, ions are supplied due to galvanic corrosion of the two electrodes. In some embodiments, the potential generated between the two electrodes permits for the reaction of ethylene with ethylene receptor. However, it is difficult to control this ion supply, and thus the design of the two-electrode system presents greater stability issues than that of the three-electrode system. In some embodiments, the measurable output of a two-electrode system tends to be either voltage or resistance. Due to the variable nature of electron supply to the system, factors such as the external environment are more likely to affect the outputs of the system.

In a three-electrode system, potential is supplied by one of the three electrodes, typically the reference electrode. Thus, there is a measurable quantity of ions supplied to the electrode system, and thus a stable baseline reading, typically of resistance. As such, any resistance change in the system is likely due to the binding event between ethylene and the ethylene receptor, generating a cleaner and more decipherable signal."

Figure 2A:
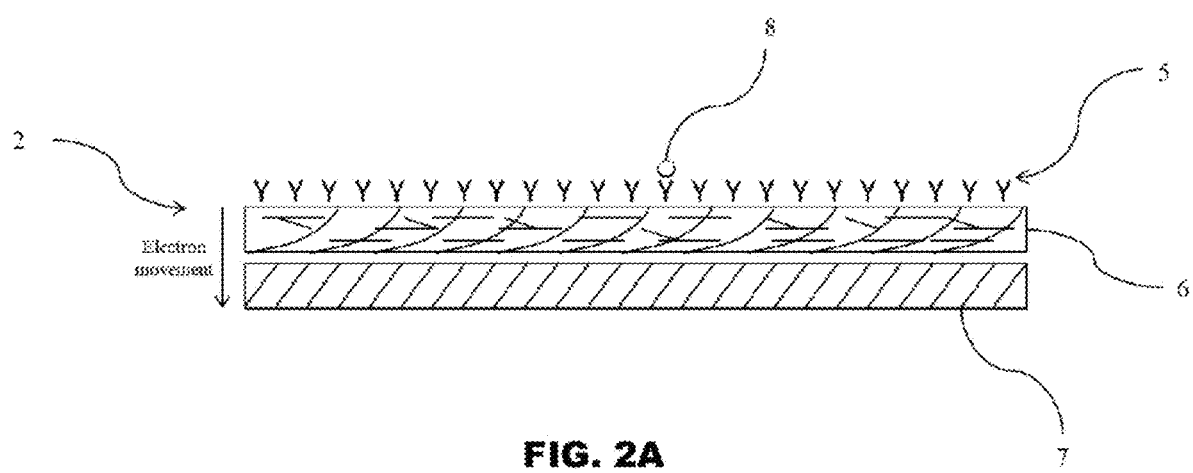
FIG. 2A illustrates a side view of a reference electrode in accordance with one embodiment of the present disclosure.

In some embodiments, and with reference to FIG. 2A, the reference electrode 2 comprises a receptor layer 5, a mediator layer 6, and a base electrode 7. The base electrode 7 may be comprised of any material known to those of ordinary skill in the art. For example, the base electrode 7 may be comprised of copper, gold, aluminum, or silver. In some embodiments, the base the electrode 7 may be comprised of indium tin oxide, gold, or silver electrodes. In some embodiments, the electrode 7 comprises a conductive metallic coating. In some embodiments, the metallic coating comprises copper and/or silver.

Figure 2B:
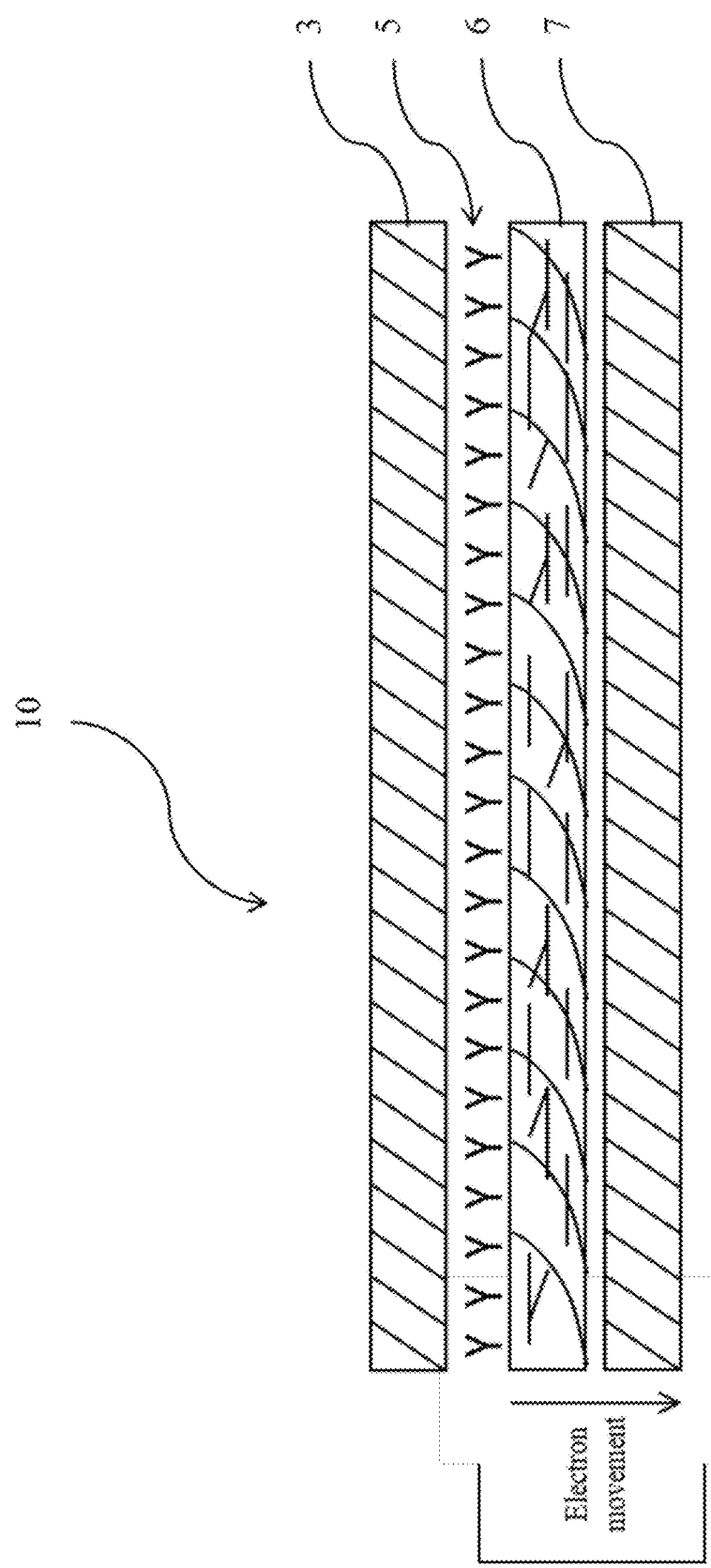
FIG. 2B illustrates a side view of a biosensor in accordance with another embodiment of the present disclosure.

FIG. 2B illustrates an alternative biosensor 10 having a reference electrode 2 including a receptor layer 5, a mediator layer 6, and an electrode 7. The biosensor depicted in FIG. 2B further includes a working electrode 3 in communication with the receptor layer 5. In some embodiments, the working electrode 3 is comprised of a material selected from gold, silver, copper, or any combination thereof. In some embodiments, the working electrode 3 of FIG. 2B is comprised of a porous material, such as metal triazolates consisting of 1H-1,2,3-triazole and divalent metal ions (Mg, Mn, Fe, Co, Cu, and Zn). In other embodiments, the working electrode of FIG. 2B includes one or more pores or punctures to facilitate the permeation of the ethylene gas through the working electrode layer 3 and to the receptor layer 5. In some embodiments, the pores or punctures may have a radius ranging from between about 2 angstroms to about 2 mm.

In some embodiments, the mediator layer 6 comprises a conductive and biocompatible material that serves to mediate electron transfer between the receptor layer and the metallic electrode. It is also believed that the mediator layer 6 serves to stabilize the components of the receptor layer, described herein. It is further believed that the mediator layer 6 facilitates crosslinking interactions with ethylene receptor proteins such that the ethylene receptor proteins become immobilized on the surface of the mediator layer 6. It is believed that electron movement resulting from reversible chemical interactions between ethylene and ethylene receptor molecules is encouraged due to the conductivity, and subsequent voltage output (between about 0 to about 7V), of the mediator layer.

In some embodiments, the mediator layer 6 comprises at least one component selected from potassium ferricyanide, ferric chloride, methyl viologen, ferrocene, cysteamine, mercaptopropionic acid, mercaptobenzoic acid, mercaptoundecanoic acid, ruthenium chloride, naphthol green, or polypyrrole. In some embodiments, the mediator layer 6 comprises (i) a first component selected from potassium ferricyanide, ferric chloride, methyl viologen, ferrocene, cysteamine, mercaptopropionic acid, mercaptobenzoic acid, mercaptoundecanoic acid, ruthenium chloride, naphthol green, or polypyrrole; and (ii) a second component.

In some embodiments, the mediator layer 6 comprises the components set forth in Table 1 below.

Table 1 provides a listing of mediator layers which may be utilized and the components of each of those mediator layers.

| Name of layer | Composition |
| --- | --- |
| Prussian Blue | about 0.05M potassium ferricyanide $3Fe(CN)_6$ and about 0.05M ferric chloride both in about 5 mmol $L^{-1}$ HCl |
| Methyl Viologen | about 10 µL glycerol, about 5 microliter nafion, about 20 microliter enzyme solution, about 10% w/v methyl viologen in about 20 mM 7.4 PBS, reticulated in saturated glutaraldehyde vapor |
| Ferrocene | about 1% (w/w) Nafion solution (in EtOH), about 0.05M ferrocene solution in DI water, about 5 mg/mL ethylene receptor solution, about 4 microliters/mL glutaraldehyde solution (25%, aqueous) |
| Cysteamine | between about 1.2 to about 2.9M cysteamine, about 2 mg/ml of enzyme |
| 3-mercaptopropionic acid | about 1.2M 3-mercaptopropionic acid, about 30 mM EDC and about 15 mM NHS, about 5 mg/mL ethylene receptor solution |
| 4-mercaptobenzoic acid | about 1.2M 4-mercaptobenzoic acid solution, about 30 mM EDC and about 15 mM NHS, about 5 mg/mL ethylene receptor solution |
| 11-mercaptoundecanoic acid | about 1.2M 11-mercaptoundecanoic acid, about 30 mM EDC and about 15 mM NHS, 5 mg/mL ethylene receptor solution |
| Ruthenium purple | about 1 mM of $RuCl_3$ solution including about 1 mM KCl |
| Naphthol Green B | about 4 mmol/L naphthol green, about 3 mg/mL ethylene receptor solution |
| (Os-(bpy)FecII) | about 8-µL of a 6-mg/ml (Os(bpy)2PVI), about 1.9 µL of a about 15-mg/mL aqueous solution of PEGDGE and about 4.8 µL of 10-mg/ml ethylene solution |
| Polypyrrole | PVDF granules in DMF (about 2% W/V) added to $FeCl_3$ to which about 2% polypyrrole is added |

In some embodiments, the receptor layer 5 comprises an ethylene receptor protein. The term "ethylene receptor" or "ethylene receptor protein," refers to ethylene receptors from any of the ethylene receptor families present in a plant. By way of example, in *Arabidopsis*, ethylene receptor proteins include ETR1, ERS1, ETR2, ERS2, and EIN4. *Zea mays* ethylene receptor proteins include ZmERS1 and ZmETR2 (including the ZmETR2 variants ZmETR9 and ZmETR40). In some embodiments, the ethylene receptor proteins are derived from the genes of *Lactuca Sativa, Bryophyta, Petunia*, and *Solanum lycopersicum* may also be used. Methods of isolating ethylene receptors are described herein, and also described in U.S. Pat. Nos. 7,951,993 and 7,105,654, the disclosures of which are hereby incorporated by reference herein in their entireties.

Ethylene receptors of the present disclosure may be isolated from any species of plant and include species homologs of the exemplary ethylene receptors. In that regard, in some embodiments, the ethylene receptor protein is naturally occurring. Examples of naturally occurring ethylene receptors include ethylene receptor 1 (ETR1) (such as derived from *ARABIDOPSIS THALIANA*), ethylene receptor 2 (ETR 2) (such as derived from *ARABIDOPSIS THALIANA*), ethylene receptor 3 (ETR3) (such as derived from *ORYZA SATIVA INDICA*), or ethylene receptor 4 (ETR4) (such as derived from *ORYZA SATIVA JAPONICA*).

In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene.

In some embodiments, the ethylene receptor has at least 80% identity to the amino acid sequence of SEQ ID NO: 1. In some embodiments, the ethylene receptor has at least 85% identity to the amino acid sequence of SEQ ID NO: 1. In some embodiments, the ethylene receptor has at least 90% identity to the amino acid sequence of SEQ ID NO: 1. In some embodiments, the ethylene receptor has at least 95% identity to the amino acid sequence of SEQ ID NO: 1. In some embodiments, the ethylene receptor has at least 96% identity to the amino acid sequence of SEQ ID NO: 1. In some embodiments, the ethylene receptor has at least 97% identity to the amino acid sequence of SEQ ID NO: 1. In some embodiments, the ethylene receptor has at least 98% identity to the amino acid sequence of SEQ ID NO: 1. In some embodiments, the ethylene receptor has at least 99% identity to the amino acid sequence of SEQ ID NO: 1. In some embodiments, the ethylene receptor comprises the amino acid sequence of SEQ ID NO: 1.

In some embodiments, the ethylene receptor has at least 80% identity to the amino acid sequence of SEQ ID NO: 2. In some embodiments, the ethylene receptor has at least 85% identity to the amino acid sequence of SEQ ID NO: 2. In some embodiments, the ethylene receptor has at least 90% identity to the amino acid sequence of SEQ ID NO: 2. In some embodiments, the ethylene receptor has at least 95% identity to the amino acid sequence of SEQ ID NO: 2. In some embodiments, the ethylene receptor has at least 96% identity to the amino acid sequence of SEQ ID NO: 2. In some embodiments, the ethylene receptor has at least 97% identity to the amino acid sequence of SEQ ID NO: 2. In some embodiments, the ethylene receptor has at least 98% identity to the amino acid sequence of SEQ ID NO: 2. In some embodiments, the ethylene receptor has at least 99% identity to the amino acid sequence of SEQ ID NO: 2. In some embodiments, the ethylene receptor comprises the amino acid sequence of SEQ ID NO: 2.

In some embodiments, the ethylene receptor has at least 80% identity to the amino acid sequence of SEQ ID NO: 3. In some embodiments, the ethylene receptor has at least 85% identity to the amino acid sequence of SEQ ID NO: 3. In some embodiments, the ethylene receptor has at least 90% identity to the amino acid sequence of SEQ ID NO: 3. In some embodiments, the ethylene receptor has at least 95% identity to the amino acid sequence of SEQ ID NO: 3. In some embodiments, the ethylene receptor has at least 96% identity to the amino acid sequence of SEQ ID NO: 3. In some embodiments, the ethylene receptor has at least 97% identity to the amino acid sequence of SEQ ID NO: 3. In some embodiments, the ethylene receptor has at least 98% identity to the amino acid sequence of SEQ ID NO: 3. In some embodiments, the ethylene receptor has at least 99% identity to the amino acid sequence of SEQ ID NO: 3. In some embodiments, the ethylene receptor comprises the amino acid sequence of SEQ ID NO: 3.

In some embodiments, the ethylene receptor has at least 80% identity to the amino acid sequence of SEQ ID NO: 4. In some embodiments, the ethylene receptor has at least 85% identity to the amino acid sequence of SEQ ID NO: 4. In some embodiments, the ethylene receptor has at least 90% identity to the amino acid sequence of SEQ ID NO: 4. In some embodiments, the ethylene receptor has at least 95% identity to the amino acid sequence of SEQ ID NO: 4. In some embodiments, the ethylene receptor has at least 96% identity to the amino acid sequence of SEQ ID NO: 4. In some embodiments, the ethylene receptor has at least 97% identity to the amino acid sequence of SEQ ID NO: 4. In some embodiments, the ethylene receptor has at least 98% identity to the amino acid sequence of SEQ ID NO: 4. In some embodiments, the ethylene receptor has at least 99% identity to the amino acid sequence of SEQ ID NO: 4. In some embodiments, the ethylene receptor comprises the amino acid sequence of SEQ ID NO: 4.

In other embodiments, the ethylene receptors also include proteins with naturally-occurring and induced mutations, including insertion, deletion, and point mutations. In yet other embodiments, the ethylene receptor protein is non-naturally occurring.

In some embodiments, between about 10 to about 1000 nanograms of ethylene receptor are protein are included within the receptor layer. In some embodiments, between about 20 to about 600 nanograms of ethylene receptor protein is included within the receptor layer. In some embodiments, between about 50 to about 300 nanograms of ethylene receptor protein is included within the receptor layer. In some embodiments, about 0.015 milligrams of ethylene receptor protein applied for every cubic centimeter of the components of the mediator layer applied. In some embodiments, about 0.04 milligrams of ethylene receptor protein are applied for every cubic centimeter of the components of the mediator layer applied. In some embodiments, about 0.002 milligrams of ethylene receptor protein are applied for every cubic centimeter of the components of the mediator layer applied.

In some embodiments, the overall thickness of the reference electrode ranges from between about 0.1 mm to about 1.5 mm. In some embodiments, each of the individual layers of the reference electrode do not exceed about 1 mm in thickness.

The ethylene receptors described above may be isolated and collected according to any process known to those of ordinary skill in the art. For example, ethylene receptor production may include the steps of (1) expressing ethylene-binding proteins in a vector host; (2) amplifying vector hosts to desired volumes; and (3) extracting/isolating desired proteins from the vector hosts. In some embodiments, gene sequences for proteins capable of binding to ethylene are expressed within a plasmid capable of being expressed by the vector host. Vector hosts are typically prokaryotic cells but may also include eukaryotic cells as well. The plasmid within which the gene sequence is inserted must be able to be translated by the vector host. Upon successful insertion of the plasmid into the vector host, the host is amplified. In bacteria, amplification typically involves culturing bacterial hosts within a broth solution for about 8 to about 12 hours. Following incubation of bacterial host with broth, the resulting bacteria is centrifuged, and protein isolation methods are performed. The means of protein extraction can be chemical, through the means of a detergent, or mechanical, such as sonication or heat treatments. An alternative means of protein extraction is by attaching a specific tag to the plasmid, such as a histidine tag, and using a column to purify his-tagged proteins. Other methods of isolating and collecting ethylene receptors are described in U.S. Patent Publication Nos. 2002/0012982A1 and U.S. Pat. No. 20020127587A1; U.S. Pat. Nos. 4,431,739, 4,366,246, and 3,585,179; and also, in EP0001929B1 and EP0001929A2, the disclosures of which are hereby incorporated by reference herein in their entireties.

Without wishing to be bound by any particular theory, it is believed that when an ethylene gas molecule 8 binds to the ethylene receptor molecules within the receptor layer 5, electron transfer occurs (see FIGS. 2A and 2B, where an ethylene molecule 8 is bound to an ethylene receptor in the receptor layer 5). In the case of the presently disclosed biosensors, the electron transfer may be passed from the receptor layer 5 to the mediator layer 6 and ultimately to the electrode 7 (see FIGS. 2A and 2B). It is further believed that multiple binding events generate electron movement that can be measured as a voltage change. The resulting voltage change can be linearly correlated to the concentration of atmospheric ethylene. It is believed that the correlation can be made by exposing the ethylene sensor to a standard of known ethylene gas concentrations and measuring the resulting voltage output. For example, over the course of a period of time, one can expose the ethylene sensor to increasing parts per million of ethylene and measure the change in voltage. These data points can then be used to estimate a linear equation correlating voltage output to ethylene binding to the sensor and resulting air concentrations of ethylene.

The biosensor 10 may be fabricated according to any method known to those of ordinary skill in the art. In some embodiments, a solution comprising the desired components of the mediator layer are drop coated onto an electrode 7 or a coated electrode 7. The components of any mediator layer 6 and the concentrations of those components relative to each other are described above in Table 1. Following the deposition of the mediator layer 6, the receptor layer 5 may be drop coated onto the mediator layer. In some embodiments, the ethylene receptor protein is included within a buffer solution and the solution is applied to a dried mediator layer 5 to provide the receptor layer 6 (upon its drying). The receptor solution typically consists of a solution with a pH range of about 7 to about 9 for the lysis of proteins. A typical lysis buffer solution contains about 50 to about 100 mM Tris-HCl, about 100 to about 300 mM NaCl, about 1 mM Dithiothreitol (DTT) or about 1% NP-40. Additionally, protease inhibitors or protease inhibitor cocktails may be added to the buffer solution following protein lysis. Alternative buffer solutions are shown in Table 2.

Table 2 lists various buffers and their corresponding pha values. Any of the ethylene receptor proteins described herein may be provided in solution with any of the buffers of Table 2.

| Buffer | pKa at 20° C. |
|---|---|
| MES | 6.15 |
| Bis-tris methane | 6.60 |
| ADA | 6.62 |
| N-(2-Acetamido)-2-aminoethanesulfonic acid (ACES) | 6.76 |
| Bis-tris propane | 6.80 |
| piperazine-N,N'-bis(2-ethanesulfonic acid) (PIPES) | 6.82 |
| 3-Morpholino-2-hydroxypropanesulfonic acid (MOPSO) | 6.95 |
| Cholamine chloride | 7.10 |
| 3-(N-morpholino)propanesulfonic acid (MOPS) | 7.15 |
| bis(2-hydroxyethyl)amine (BES) | 7.17 |
| 2-[[1,3-dihydroxy-2-(hydroxymethyl)propan-2-yl]amino]ethanesulfonic acid (TES) | 7.5 |
| (4-(2-hydroxyethyl)-1-piperazineethanesulfonic acid) (HEPES) | 7.55 |
| [3-Bis(2-hydroxyethyl) amino-2-hydroxypropane-1-sulfonic acid] (DIPSO) | 7.6 |
| 4-(N-Morpholino)butanesulfonic acid (MOBS) | 7.6 |
| Acetamidoglycine | 7.7 |
| 3-[[1,3-dihydroxy-2-(hydroxymethyl)propan-2-yl]amino]-2-hydroxypropane-1-sulfonic acid (TAPSO) | 7.6 |
| tris(hydroxymethyl)aminomethane - acetate-Ethylenediaminetetraacetic acid (TEA) | 7.8 |
| [Piperazine-1,4-bis(2-hydroxy-3-propanesulfonic acid),dihydrate] (POPSO) | 7.85 |
| ((2-Hydroxyethyl)-piperazine-N-2-hydroxypropanesulfonic acid) (HEPPSO) | 7.9 |
| EPS | 8.0 |
| 3-[4-(2-Hydroxyethyl)piperazin-1-yl]propane-1-sulfonic acid (HEPPS) | 8.1 |
| N-(2-Hydroxy-1,1-bis(hydroxymethyl)ethyl)glycine (Tricine) | 8.15 |
| tris(hydroxymethyl)aminomethane | 8.2 |
| Glycinamide | 8.2 |
| Glycylglycine | 8.2 |
| N-(2-Hydroxyethyl)piperazine-N'-(4-butanesulfonic acid) (HEPBS) | 8.3 |
| 2-(Bis(2-hydroxyethyl)amino)acetic acid (Bicine) | 8.35 |
| 3-{[1,3-dihydroxy-2-(hydroxymethyl)propan-2-yl]amino}propane-1-sulfonic acid (TAPS) | 8.55 |
| 2-Amino-2-Methyl-1-Propanol (AMP) | 8.8 |
| 2-(Cyclohexylamino)ethanesulfonic acid (CHES) | 9.3 |
| ((1,1-Dimethyl-2-hydroxyethyl)amino)-2-hydroxypropanesulfonic acid sodium salt (AMPSO) | 9.0 |
| N-cyclohexyl-2-hydroxyl-3-aminopropanesulfonic acid (CAPSO) | 9.6 |
| 3-(Cyclohexylamino)-1-propanesulfonic acid (CAPS) | 10.4 |

Figure 3A:
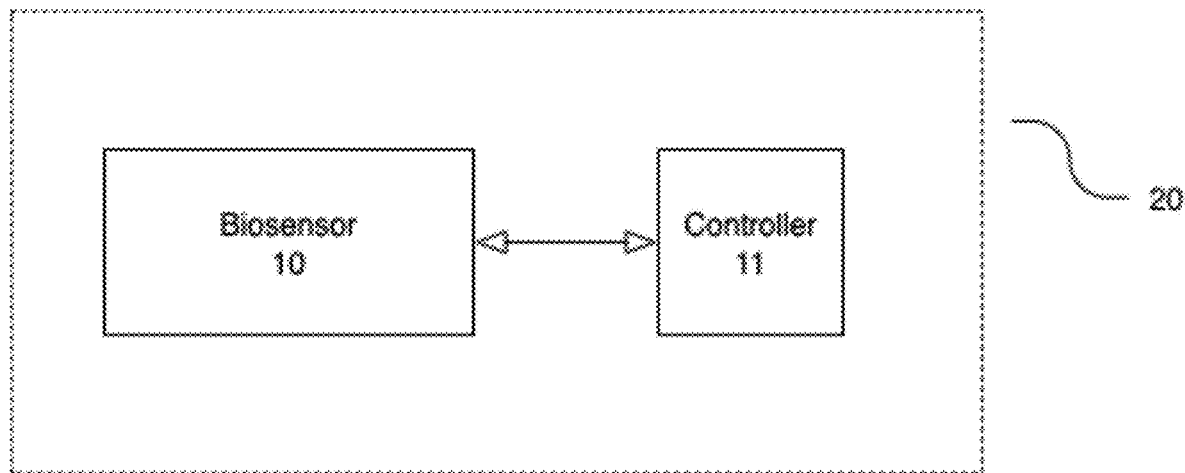
FIG. 3A illustrates a schematic of a biosensor in communication with a controller in accordance with one embodiment of the present disclosure.
Figure 3B:
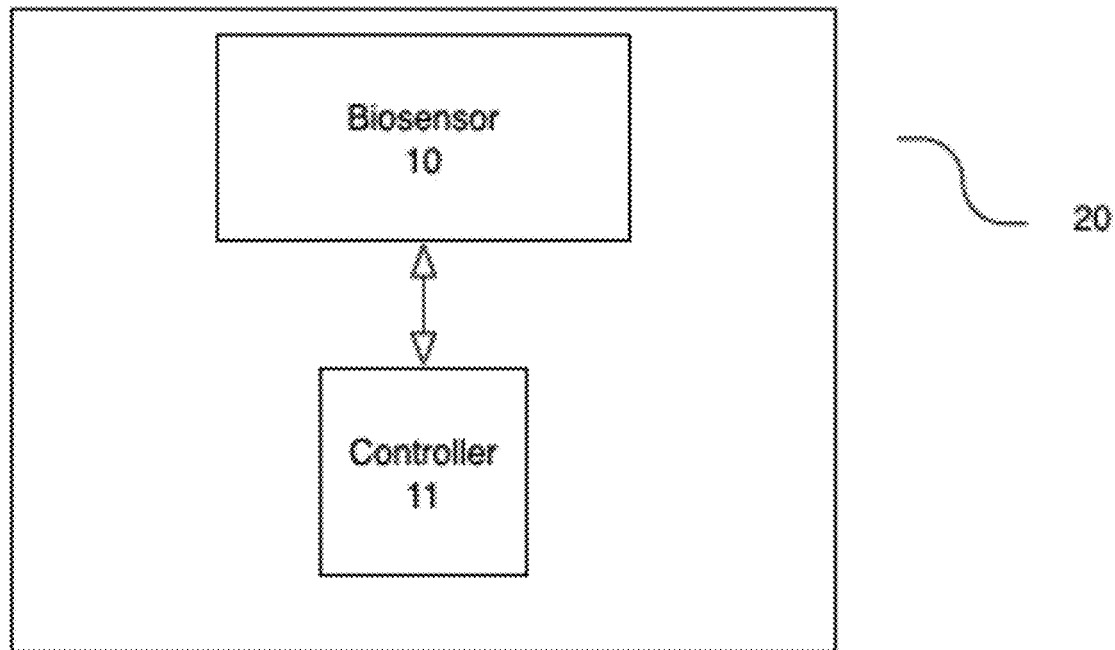
FIG. 3B illustrates a schematic of a sensor unit comprising a biosensor and a controller in accordance with one embodiment of the present disclosure.
Figure 3C:
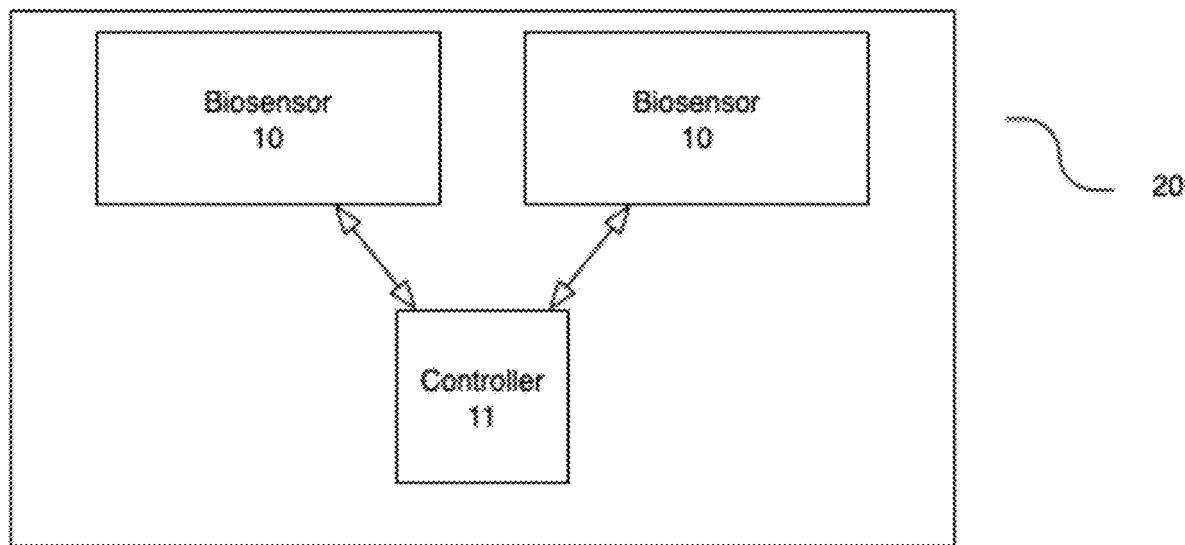
FIG. 3C illustrates a schematic of a sensor unit comprising a plurality of biosensors and a controller in accordance with one embodiment of the present disclosure.

In another aspect of the present disclosure is a sensor unit 20 incorporating one or more of the biosensors 10 of the present disclosure. As depicted in FIGS. 3A and 3B, the sensor unit 20 may be coupled to a controller 11 such that current changes due to the binding of ethylene to the ethylene receptor molecules may be measured and/or recorded. In some embodiments, the sensor unit 20 comprises a biosensor 10 and a controller 11, where the biosensor 10 and controller 11 are provided in separate housings (FIG. 3A). Alternatively, the sensor unit 20 comprises a biosensor 10 and a controller 11, where the biosensor 10 and controller 11 are coupled together, such as within the same housing or where both are provided on a chip. FIG. 3C illustrates a sensor unit 20 comprising at least two biosensors 10, each independently in communication with a controller 11. While FIG. 3C illustrates a sensor unit 20 comprising only two biosensors 10, the skilled artisan will appreciate that any number of biosensors 10 may be coupled to a single controller 11, e.g. 3, 4, 5, 10, or more biosensors.

Figure 3D:
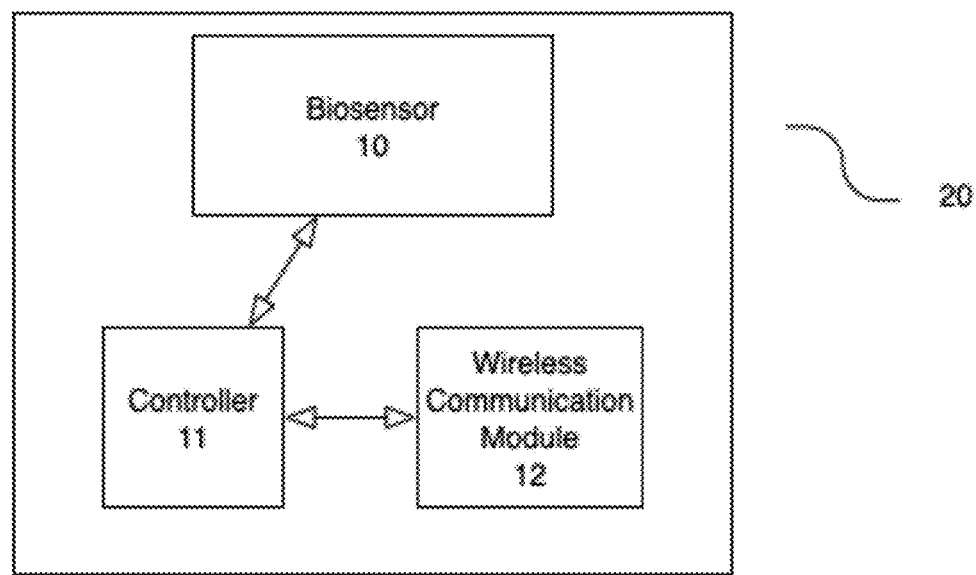
FIG. 3D illustrates a schematic of a sensor unit comprising a biosensor, a controller, and a wireless communications module in accordance with one embodiment of the present disclosure.
Figure 3E:
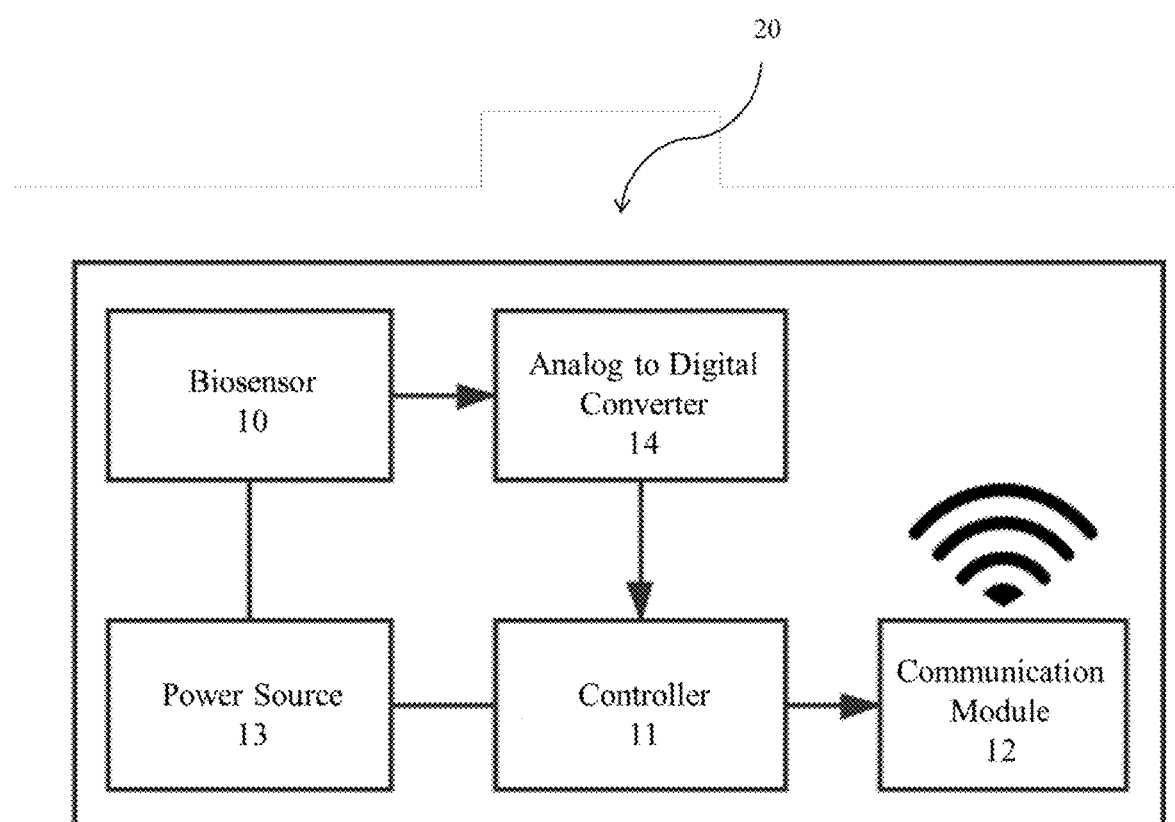
FIG. 3E illustrates a schematic of a sensor unit comprising a biosensor, a controller, a power source, an analog to digital converter, and a wireless communications module in accordance with one embodiment of the present disclosure.

In some embodiments, the controller includes a wireless communication module. In some embodiments, the wireless communications module is included within the controller 11 (i.e. within the same chip or module). In other embodiments, and with reference to FIG. 3D, the wireless communications module 12 is separate from controller 11. In some embodiments, and with reference to FIG. 3E, sensor unit 20 may comprise one or more biosensors 10; a power supply 13; a wireless communication module 12; and an analog to digital converter 14. In some embodiments, each sensor unit 20 may further comprise a memory module, e.g. volatile (e.g. RAM, etc.) and non-volatile (e.g. ROM, flash-memory, etc.) memory, additional processors or programmable circuits, other communication means (e.g. wired network communication), timers, oscillators, motion detectors, GPS modules, or any other helper device or circuit.

Figure 4:
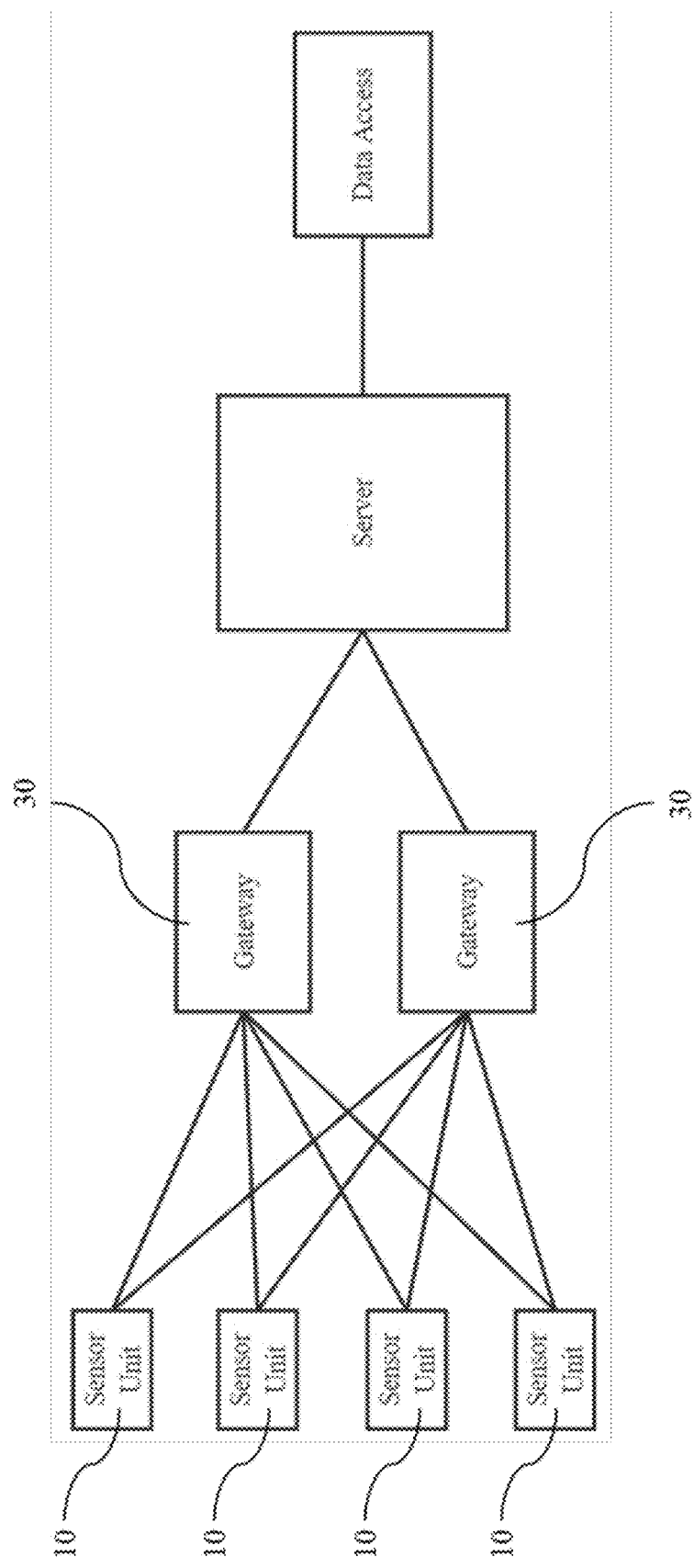
FIG. 4 illustrates a plurality of sensor units in wireless communication with a wireless gateway in accordance with one embodiment of the present disclosure.

In some embodiments, multiple sensor units 20 may be in wireless communication with each other or in wireless communication with a gateway 30, a server 31, storage device, etc. (see FIG. 4). In some embodiments, each sensor unit 20 may communicate via infrared pulses, radio waves, ultrasonic waves, or another wireless communication medium. In some embodiments, wireless communications are through a standard protocol, for example a Zigbee mesh network, LoRaWAN, 802.11 WiFi, or Bluetooth. Proprietary solutions could also be used. Wireless communication protocols will typically be accomplished using integrated circuits or modules specifically designed for the purpose. Modules appropriate for the purpose include those manufactured by, for example, Digi International, Synapse Wireless, Motorola, or Panasonic.

In some embodiments, the sensor units 20 have means for communicating with each other, with the wireless gateway, and/or with other network units, thus establishing a sensor network of any suitable kind. A network of the sensor units (a "sensor network") may be more or less organized, with none or any level of central control. In some embodiments, the wireless gateway may act as a common network controller for organizing the wireless sensors, e.g. by assigning IP-addresses in an IP network configuration. In some embodiments, the wireless gateway is a network unit that avails access in some sense between the individual sensor units of the sensor network and one or more external units. The wireless gateway may, for example, comprise a conventional wireless network gateway hardware for establishing access and routing between different networks, e.g. the wireless sensors with WiFi capabilities and the Internet or any other network, or e.g. a GSM or other cellular network communication unit. The wireless gateway may thus comprise one or more of the functionalities and tasks of conventional gateways, access points, routers, bridges, network address assigning or resolving, security controllers, web servers, etc. In some embodiments, the wireless gateway also carries out the task of collecting and possibly refining data and information from the individual sensor units of the sensor network.

In addition, the wireless gateway 30 may comprise a sensor unit 20 or it may be a sensor-free unit entirely dedicated to collecting data from all the sensor units 20. The wireless gateway 30 may further comprise positioning means for obtaining an initial position for itself, e.g. by means of a GPS unit which is feasible if located outside the biomass and heavy buildings or containers. The gateway 30 may also be provided with its position manually by the user, or it may simply be defining the center of the world as far as the sensor units 20 are concerned, i.e. the origin or other reference position in their positioning grid.

In some embodiments, the biosensor 10 is calibrated by exposing it to fixed concentrations of ethylene, and the voltage is measured. A linear correlation between voltage and ethylene concentration is established, and this standard can be used to measure ethylene concentrations outside of the tested range.

EXAMPLES

Receptor Isolation

Ethylene receptor genes expressed via plasmid, such as ETR1, ETR2, or ETR3, were transformed into bacteria. Following transformation, bacteria were streaked onto an agar plate, and after 12-24 hrs of incubation colonies form upon the surface. If using an antibacterial resistance plasmid, the agar should also contain the selected antibiotic. Colonies were picked and sequenced to ensure proper insertion of plasmidic DNA. Following the selection of properly expressing colonies, bacteria were amplified in LB broth for the desired yield. Typically, bacteria are grown in between 2 mL-1 L of broth for 12-18 hrs at 37 degrees Celsius.

Following bacterial growth, the bacteria were centrifuged, and the LB broth was removed. The bacterial pellet was treated with a protein extraction agent, and protein extraction was performed according to protocols specific to the reagent used. Specific protein isolation could be performed via centrifugation, if the protein is of known concentration, via antibody pulldown protocols, or by amending the plasmidic sequence to include a specific binding site, such as a poly-histidine tail, and using an affinity column to isolate the protein.

Biosensor Testing 1

Figure 5:
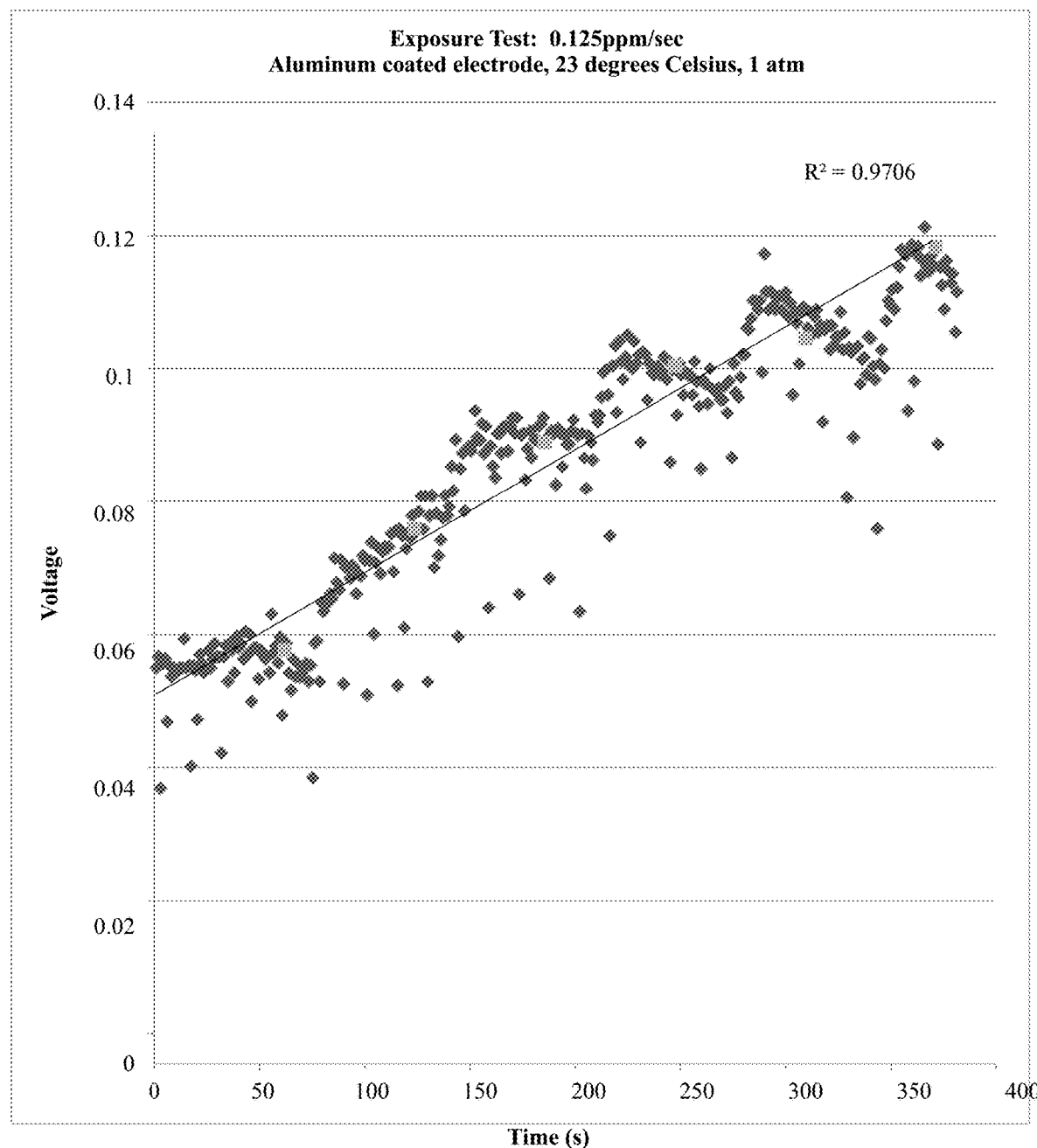
FIG. 5 provides a graph setting forth the results of an exposure test to about 7.5 ppm/min or ethylene. An ethylene biosensor was exposed to about 7.5 ppm/min of ethylene gas at standard atmospheric conditions within a confined about 5 L container. The voltage output correlated in a statistically significant manner to the overall ethylene concentration within the container.
Figure 6:
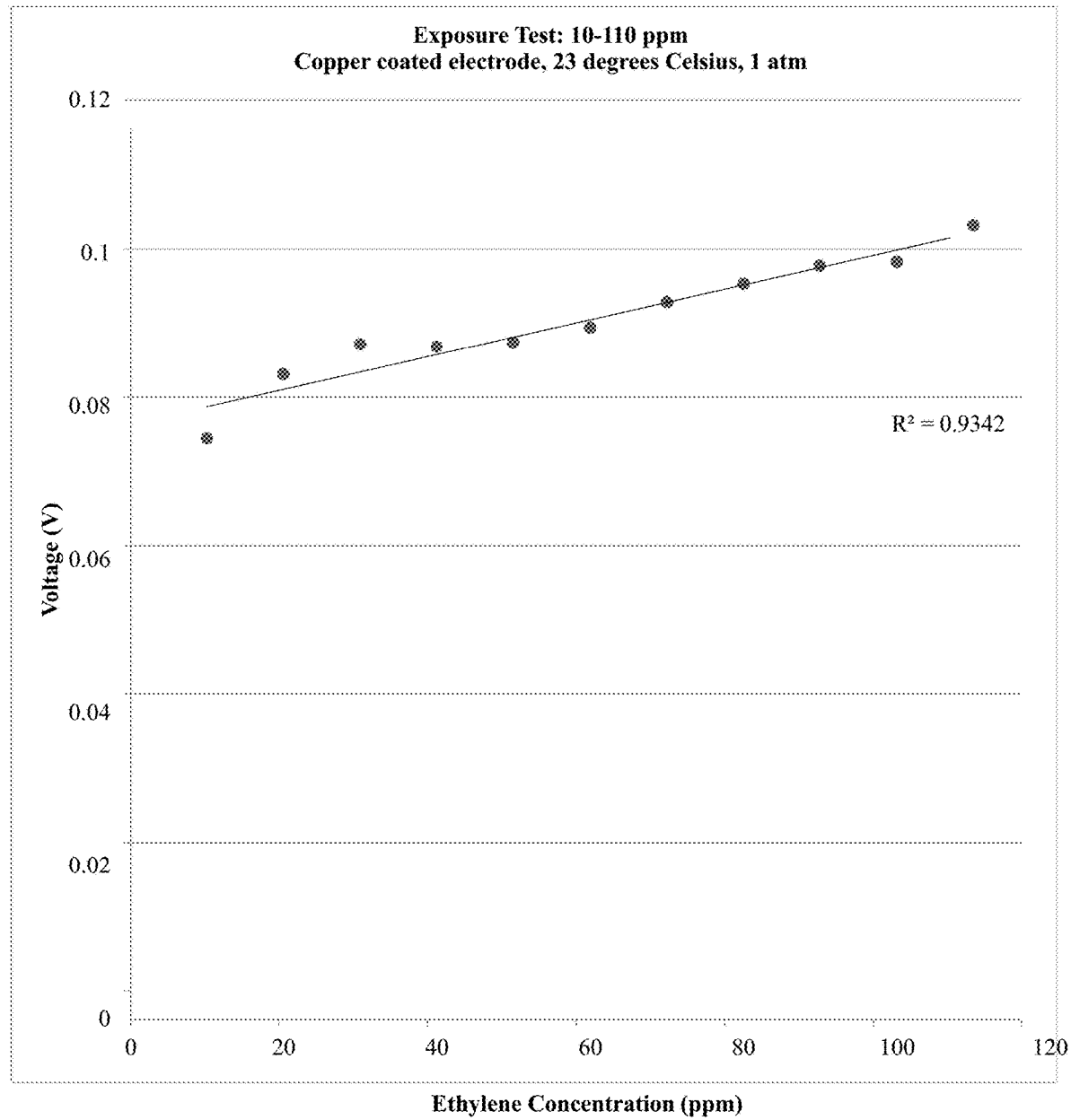
FIG. 6 provides a graph setting forth the results of an exposure test for about 10 to about 110 ppm of ethylene under standard atmospheric conditions. A biosensor was exposed from about 10 to about 110 ppm of ethylene. A reading was taken about at every 10 ppm.
Figure 7:
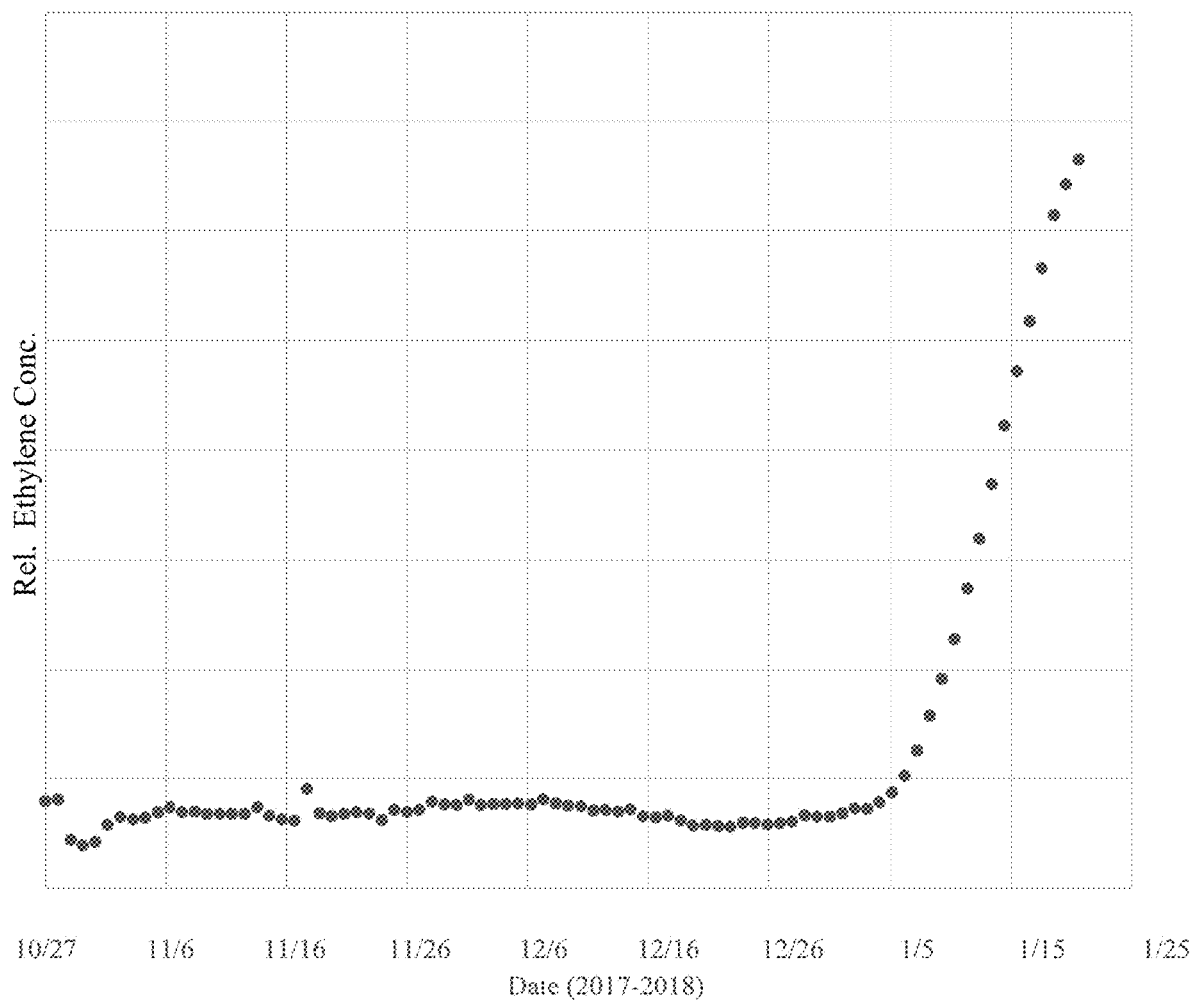
FIG. 7 provides a graph setting forth the results of ethylene testing using a biosensor of the present disclosure, where the ethylene concentration spike corresponds to quality control data, which indicated a change in fruit maturity.

An ethylene biosensor including the components described herein (about 200 μL of about 10% pyrrole mediator layer with about 0.015 mg/mm of *Arabidopsis* ETR1 upon an about 2 square inch copper electrode) was placed into a 5 L airtight vacuum chamber at standard atmospheric conditions. A biosensor consisting of an aluminum electrode, pyrrole mediator, and 100 ng of protein was exposed to ethylene at a concentration of about 0.125 ppm/sec for about 375 seconds. The voltage output of the sensor was measured continuously during ethylene exposure (see FIG. 5). Voltage outputs correlated linearly with linear exposure of ethylene to the biosensor, establishing a standard relationship between voltage and ethylene concentration. This correlation was statistically significant, with an R-squared value of about 0.97. The resulting equation generated by correlating ethylene exposure to voltage output, can be used to predict ethylene concentrations outside of the standard's bounds. This standard was replicated for a greater range of ethylene concentrations in FIG. 6, which analyzed the performance of a biosensor with a copper electrode, about 100 μL of pyrrole mediator, and about 100 μL of protein. This figure supported the linear relationship between voltage and ethylene concentration for a greater range of ethylene concentrations.

Biosensor Testing 2

The sensor (about 200 μL of an about 5% pyrrole mediator with about 0.015 mg/mm of *Arabidopsis* ETR1 upon a two square inch aluminum electrode) was tested within controlled atmosphere storage of apples. Depicts an experiment conducted for a period of 82 days within a controlled atmosphere storage room kept at 1 degree Celsius, about 2% O2, and about 0.6% $CO_2$, with 2,000 bins of honey crisp apples. On day 70, the relative ethylene concentration within the controlled atmosphere storage room spiked, indicating the beginning of senescence for the fruit within the storage room (see FIG. 8). Using this data, a prediction was made for the room based on the senescence curve of honey crisp apples that the storage room had 1-2 months prior to experiencing significant maturity related losses due to fruit senescence. This data correlated with quality control data of fruit samples pulled from the room following its opening. This result indicates the predictive ability of an ethylene sensor in determining fruit senescence, which may be used to mitigate losses within the food supply chain.

Additional Embodiment 1: A biosensor comprising: (a) a reference electrode comprising (i) a mediator layer deposited on a base electrode; and (ii) a receptor layer deposited on the mediator layer, wherein the receptor layer comprises an ethylene receptor; (b) a working electrode in communication with the reference electrode; and (c) a counter electrode.

Additional Embodiment 2: The biosensor of additional embodiment 1, wherein the base electrode is comprised of a material selected from the group consisting of copper and silver.

Additional Embodiment 3: The biosensor of additional embodiment 1, wherein the base electrode comprises a coating of a material selected from the group consisting of copper and silver.

Additional Embodiment 4: The biosensor of additional embodiment 1, wherein the ethylene receptor comprises a nucleotide sequence having at least 90% sequence identity to a wild-type polynucleotide sequence of an ethylene receptor gene.

Additional Embodiment 5: The biosensor of additional embodiment 1, wherein the ethylene receptor is derived from *Zea mays* or *Arabidopsis*.

Additional Embodiment 6: The biosensor of additional embodiment 1, wherein the ethylene receptor comprises an amino acid sequence having at least 90% identity to that of SEQ ID NO: 1.

Additional Embodiment 7: The biosensor of additional embodiment 1, wherein the ethylene receptor comprises an amino acid sequence having at least 90% identity to that of SEQ ID NO: 2.

Additional Embodiment 8: The biosensor of additional embodiment 1, wherein the ethylene receptor comprises an amino acid sequence having at least 90% identity to that of SEQ ID NO: 3.

Additional Embodiment 9: The biosensor of additional embodiment 1, wherein the ethylene receptor comprises an amino acid sequence having at least 90% identity to that of SEQ ID NO: 4.

Additional Embodiment 10: The biosensor of additional embodiment 1, wherein the receptor layer comprises between about 10 to about 1000 nanograms of ethylene receptor.

Additional Embodiment 11: The biosensor of additional embodiment 1, wherein the mediator layer comprises at least one of potassium ferricyanide, methyl viologen, ferrocene, cystamine, mercaptopropionic acid, mercaptobenzoic acid, mercaptoundecanoic acid, ruthenium chloride, naphthol green, or polypyrrole.

Additional Embodiment 12: A stack comprising: (a) a mediator layer, and (b) a receptor layer in contact with the mediator layer, wherein the receptor layer comprises one or more ethylene receptor proteins.

Additional Embodiment 13: The stack of additional embodiment 12, wherein the one or more ethylene receptor proteins are selected from the group consisting of ETR1, ETR2, ETR3, and ETR4.

Additional Embodiment 14: The stack of additional embodiment 12, wherein the one or more ethylene receptor proteins comprises an amino acid sequence having at least 90% identity to any of SEQ ID NOS: 1-4.

Additional Embodiment 15: The stack of additional embodiment 12, wherein the receptor layer comprises between about 0.038 mg/mm to about 0.38 mg/mm nanograms of ethylene receptor proteins.

Additional Embodiment 16: The stack of additional embodiment 12, wherein the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

Additional Embodiment 17: A reference electrode comprising the stack of any one of additional embodiments 12 to 16 deposited on a base electrode.

Additional Embodiment 18: The reference electrode of additional embodiment 17, wherein the base electrode comprises a coating including copper or silver.

Additional Embodiment 19: A biosensor comprising the reference electrode of any one of additional embodiments 17-18; and a working electrode in communication with the reference electrode.

Additional Embodiment 20: A sensor unit comprising the biosensor of any one of additional embodiments 1 to 11 and 19; and a controller in communication with the biosensor.

Additional Embodiment 21: The sensor unit of additional embodiment 20, wherein the controller comprises a communication module.

Additional Embodiment 22: The sensor unit of additional embodiment 21, wherein the communication module is a wireless communication module.

Additional Embodiment 23: A system comprising a plurality of the sensor units of additional embodiment 22, wherein the plurality of sensor units are each independently in wireless communication with a receiver module, gateway, or storage module.

Additional Embodiment 24: A container comprising at least one of the sensor units of any one of additional embodiments 20 to 22.

Additional Embodiment 25: A biosensor comprising: (a) a reference electrode comprising (i) a mediator layer deposited on a base electrode; and (ii) a receptor layer deposited on the mediator layer, wherein the receptor layer comprises an ethylene receptor; and (b) a working electrode in communication with the reference electrode.

Additional Embodiment 26: The biosensor of additional embodiment 25, wherein the base electrode is comprised of a material selected from the group consisting of copper and silver.

Additional Embodiment 27: The biosensor of additional embodiment 25, wherein the base electrode comprises a coating of a material selected from the group consisting of copper and silver.

Additional Embodiment 28: The biosensor of additional embodiment 25, wherein the ethylene receptor comprises a nucleotide sequence having at least 90% sequence identity to a wild-type polynucleotide sequence of an ethylene receptor gene.

Additional Embodiment 29: The biosensor of additional embodiment 25, wherein the ethylene receptor is derived from *Zea mays* or *Arabidopsis*.

Additional Embodiment 30: The biosensor of additional embodiment 25, wherein the ethylene receptor comprises an amino acid sequence having at least 90% identity to that of SEQ ID NO: 1.

Additional Embodiment 31: The biosensor of additional embodiment 25, wherein the ethylene receptor comprises an amino acid sequence having at least 90% identity to that of SEQ ID NO: 2.

Additional Embodiment 32: The biosensor of additional embodiment 25, wherein the ethylene receptor comprises an amino acid sequence having at least 90% identity to that of SEQ ID NO: 3.

Additional Embodiment 33: The biosensor of additional embodiment 25, wherein the ethylene receptor comprises an amino acid sequence having at least 90% identity to that of SEQ ID NO: 4.

Additional Embodiment 34: The biosensor of additional embodiment 25, wherein the receptor layer comprises between about 10 to about 1000 nanograms of ethylene receptor.

Additional Embodiment 35: The biosensor of additional embodiment 25, wherein the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

Additional Embodiment 36: A stack comprising: (a) a mediator layer, and (b) a receptor layer in contact with the mediator layer, wherein the receptor layer comprises an ethylene receptor protein.

Additional Embodiment 37: The stack of additional embodiment 36, wherein the ethylene receptor protein is selected from the group consisting of ETR1, ETR2, ETR3, and ETR4.

Additional Embodiment 38: The stack of additional embodiment 36, wherein the ethylene receptor protein comprises an amino acid sequence having at least 90% identity to any of SEQ ID NOS: 1-4.

Additional Embodiment 39: The stack of additional embodiment 36, wherein the receptor layer comprises between about 0.038 mg/mm to about 0.38 mg/mm nanograms of ethylene receptor proteins.

Additional Embodiment 40: The stack of additional embodiment 36, wherein the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

Additional Embodiment 41: A reference electrode comprising the stack of any one of additional embodiments 12 to 16 deposited on a base electrode.

Additional Embodiment 42: The reference electrode of additional embodiment 41, wherein the base electrode comprises a coating including copper or silver.

Additional Embodiment 43: A biosensor comprising the reference electrode of any one of additional embodiments 17-18; and a working electrode in communication with the reference electrode.

Additional Embodiment 44: A sensor unit comprising the biosensor of any one of additional embodiments 1 to 11 and 19; and a controller in communication with the biosensor.

Additional Embodiment 45: The sensor unit of additional embodiment 44, wherein the controller comprises a communication module.

Additional Embodiment 46: The sensor unit of additional embodiment 45, wherein the communication module is a wireless communication module.

Additional Embodiment 47: A system comprising a plurality of the sensor units of additional embodiment 22, wherein the plurality of sensor units are each independently in wireless communication with a receiver module, gateway, or storage module.

Additional Embodiment 48: A container comprising at least one of the sensor units of any one of additional embodiments 44 to 46.

---

The invention claimed is:

1. A system comprising: at least two sensor units, where each of the at least two sensor units comprise one or more biosensors and a controller in communication with the one or more biosensors, wherein the one or more biosensors comprise: (a) a reference electrode comprising (i) a mediator layer deposited on a base electrode; and (ii) a protein receptor layer deposited on the mediator layer, wherein the protein receptor layer comprises an ethylene receptor protein; and (b) a counter electrode in communication with the reference electrode.

2. The system of claim 1, wherein the at least two sensor units comprise a communication module.

3. The system of claim 2, wherein the communication module is a wireless communication module.

4. The system of claim 2, wherein the communication module is separate from the controller.

5. The system of claim 2, wherein the communication module is integrated with the controller.

6. The system of claim 1, further comprising an analog to digital converter.

7. The system of claim 1, further comprising at least one memory.

8. The system of claim 1, wherein the ethylene receptor protein comprises a nucleotide sequence having at least 80% sequence identity to a wild-type polynucleotide sequence of an ethylene receptor gene.

9. The system of claim 1, wherein the ethylene receptor protein comprises an amino acid sequence having at least 80% sequence identity to any one of SEQ ID NOS: 1-4.

10. The system of claim 1, wherein the ethylene receptor protein comprises an amino acid sequence having at least 85% sequence identity to any one of SEQ ID NOS: 1-4.

11. The system of claim 1, wherein the biosensor further comprises a working electrode.

12. The system of claim 1, further comprises at least one gateway.

13. The system of claim 12, wherein the at least one gateway is a wireless gateway.

14. The system of claim 1, wherein each of the at least two sensor units are communicatively coupled to each other through a wireless communication module.

15. The system of claim 1, wherein a first of the at least two sensor units comprises two or more biosensors.

16. A container comprising at least one sensor unit, wherein the at least one sensor comprises one or more biosensors and a controller in communication with the one or more biosensors, wherein the one or more biosensors comprise: (a) a reference electrode comprising (i) a mediator layer deposited on a base electrode; and (ii) a protein receptor layer deposited on the mediator layer, wherein the protein receptor layer comprises an ethylene receptor protein; and (b) a counter electrode in communication with the reference electrode.

17. The container of claim 16, wherein the ethylene receptor protein comprises an amino acid sequence having at least 80% sequence identity to any one of SEQ ID NOS: 1-4.

18. A storage room comprising at least one sensor unit, wherein the at least one sensor comprises one or more biosensors and a controller in communication with the one or more biosensors, wherein the one or more biosensors comprise: (a) a reference electrode comprising (i) a mediator layer deposited on a base electrode; and (ii) a protein receptor layer deposited on the mediator layer, wherein the protein receptor layer comprises an ethylene receptor protein; and (b) a counter electrode in communication with the reference electrode.

19. The storage room of claim 18, wherein the ethylene receptor protein comprises an amino acid sequence having at least 80% sequence identity to any one of SEQ ID NOS: 1-4.

20. The storage room of claim 18, wherein the storage room comprises at least two sensor units.

* * * * *